United States Patent [19]

Kuester

[11] Patent Number: 4,678,860

[45] Date of Patent: Jul. 7, 1987

[54] PROCESS OF PRODUCING LIQUID HYDROCARBON FUELS FROM BIOMASS

[75] Inventor: James L. Kuester, Scottsdale, Ariz.

[73] Assignee: Arizona Board of Regents, Tempe, Ariz.

[21] Appl. No.: 784,269

[22] Filed: Oct. 4, 1985

[51] Int. Cl.[4] .............................................. C10L 1/16
[52] U.S. Cl. .......................................... 585/14; 44/53; 44/56; 518/704; 568/909; 585/310; 585/240
[58] Field of Search .................. 518/704; 568/909; 44/53, 56; 585/240, 310, 14

[56] References Cited

U.S. PATENT DOCUMENTS

| | | | |
|---|---|---|---|
| 4,396,786 | 8/1983 | Bond et al. | 44/50 |
| 4,451,680 | 5/1984 | Knifton | 568/909 |
| 4,487,972 | 12/1984 | Haag et al. | 568/909 |
| 4,579,985 | 4/1986 | Minderhoud et al. | 518/704 |
| 4,582,630 | 4/1986 | Quang et al. | 518/704 |

Primary Examiner—Jacqueline V. Howard
Attorney, Agent, or Firm—Richard R. Mybeck

[57] ABSTRACT

A continuous thermochemical indirect liquefaction process to convert various biomass materials into diesel-type transportation fuels which fuels are compatible with current engine designs and distribution systems comprising feeding said biomass into a circulating solid fluidized bed gasification system to produce a synthesis gas containing olefins, hydrogen and carbon monoxide and thereafter introducing the synthesis gas into a catalytic liquefaction system to convert the synthesis gas into liquid hydrocarbon fuel consisting essentially of $C_7$–$C_{17}$ paraffinic hydrocarbons having cetane indices of 50+.

23 Claims, 1 Drawing Figure

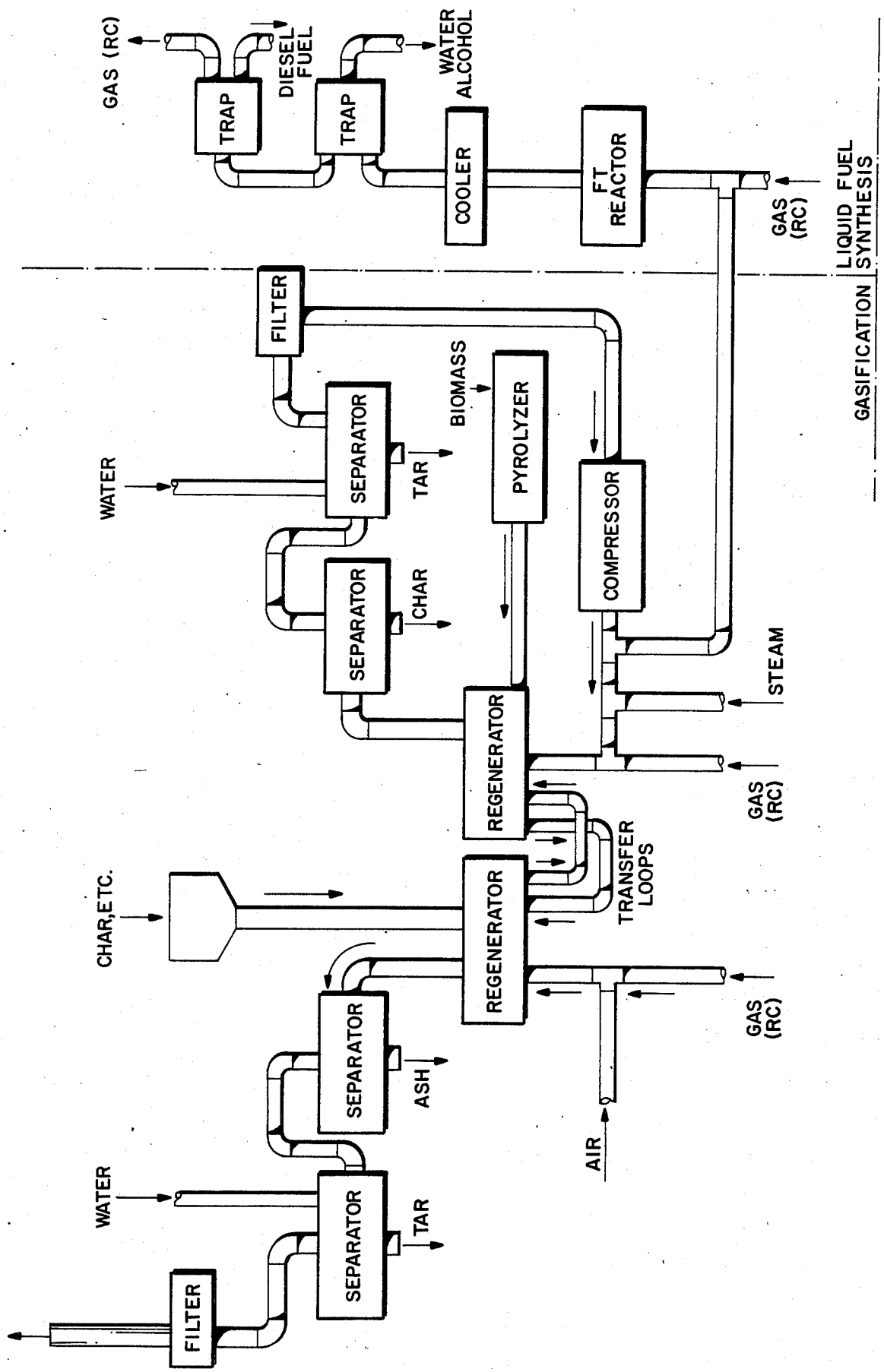

4,678,860

PROCESS OF PRODUCING LIQUID HYDROCARBON FUELS FROM BIOMASS

INTRODUCTION

This invention was made with government suport under contract No. DE-AC02-76 CS40202 awarded by the Department of Energy. The United States government has certain rights in this invention.

The present invention relates generally to the production of liquid hydrocarbon fuel and more particularly to an economically viable process for converting selected biomass materials by indirect liquefication into diesel fuel and comparable energy sources.

BACKGROUND OF INVENTION

From the moment man realized that his sublime dependancy upon the existance of an inexhaustable supply of fossil fuel was folly, there has been an intense drive to convert other hydrocarbon sources into combustible fuels.

Projects have arisen virtually throughout the world in an attempt to convert vegetable oils, forestry residues and other forms of renewable organic materials and of organic wastes into various energy-releasing compounds. Even the U.S. government entered the picture during the period following the OPEC embargo to develop alternative liquidfuels from crops specifically grown for conversion into such fuels. However, this effort was principally directed to the production of methanol and ethanol which required significant modifications to existing engine systems and new dispensing methods.

These projects have failed to provide a commercially efficacious basis upon which to build an economically viable upscale for the production of a fossil fuel alternative and a great need still exists for the development of production processes utilizing readily renewable materials, e.g., harvested crops, as a source material.

SUMMARY OF INVENTION

The present invention provides a method whereby a variety of indigenous biomass materials are demonstrated to be convertible into a viable and economically efficient alternative, such as No. 2 diesel fuel, kerosene, JP-4 jet fuel and like fuels, all of which are fully compatible with existing engine designs and distribution systems. Further, the method of the present invention is capable of both a regional production facility as well as use in an idiosyncratic installation whereby the fuel produced provides the energy required to conduct the principal operation from which the biomass is derived.

In the context of this disclosure "biomass" and "biomass materials" are used interchangeably to define any organic material derived by photosynthesis which has not been converted into a fossil fuel (e.g., petroleum, coal etc.). The feedstock utilized in the present invention will include not only biomass but also mixtures of biomass with other materials such as fossil fuels and materials derived from fossil fuels such as synthetic polymers and the like.

More particularly the present invention comprises a method for converting preselected and often indigeneous biomass into diesel fuel or similar hydrocarbon fuels by a continuous indirect liquefaction process in which the decomposition of the biomass feed stock in a circulating solid fluidized bed system or other appropriate chemical reactor conversion system produces a synthesis gas containing olefins, hydrogen and carbon monoxide which in turn is converted by catalytic liquefaction into the desired fuel having a cetene rating of 50+. The process of this invention is capable under the parameters hereinafter specified of obtaining yields of 30-50 gallons of fuel per ton of feedstock using relatively inexpensive cobalt/alumina impregnated catalysts or similar catalyst formulations. The fuel produced hereby, as will hereafter be shown, is capable of use in those engines (unmodified) currently fueled by No. 2 diesel, kerosene, JP-4 and like hydrocarbon fuels.

Accordingly, it is a prime object of the present invention to provide a new and improved process for producing transportation grade liquid hydrocarbon fuels which is scientifically sound and economically viable using renewable or waste cellulosic or synthetic polymer feedstocks or mixtures thereof.

Another object of the present invention to provide a new and improved process of converting renewable or waste biomass materials into useful liquid hydrocarbon fuels by indirect liquefaction.

A further object of the present invention is to provide a new and improved process of converting biomass materials into useful liquid hydrocarbon fuels which process is capable of providing economically viable production facilities for the small onsight users as well as for a regional distribution complex.

A still further object of the present invention is to provide a novel and unique process for producing liquid hydrocarbon fuels equivalent to those currently derived from crude petroleum without depending upon crude petroleum as a source material.

Still another object of the present invention is to provide a new and improved process of converting biomass feedstock into liquid fuel hydrocarbons which is ecologically sound and environmentally acceptable irrespective of situs.

These and still further objects as shall hereinafter appear are readily fulfilled by the present invention in a remarkably unexpected manner as will be readily discerned from the following detailed description of an exemplary embodiment thereof especially when read in conjunction with the accompanying drawing.

DESCRIPTION OF DRAWING

In the drawing is shown:

A schematic flow diagram illustrating a method of producing liquid hydrocarbon fuel from biomass materials in accordance with the present invention.

DESCRIPTION OF PREFERRED EMBODIMENT

A biomass feedstock, selected from forest residues, agricultural and/or industrial waste and the like (hereafter described in detail) is comminuted in size if necessary using conventional comminuting equipment, to particles of appropriate diameter and disposed in a suitable hopper for introduction to the system. Material prepared in excess of immediate needs is storeable in appropriate housings or silos which are installed adjacent the conversion facility as needed.

Referring to the drawing, the process is initiated by delivering feed stock from the hopper to the pyrolyzer on either a continuous or a batch basis as exigencies require. "Pyrolyzer" as used herein, refers to an appropriate chemically reactive conversion system which is capable of decomposing the feedstock into the desired synthesis gas. As shown, a gravity feeder may be utilized. Alternatively, continuous feeders having a variable feed rate of from 0 to about 2250 pounds per hour may also be employed.

In one practice of the present invention, feedstock fines will be stored separately from the coarser material to prevent dusting and to permit forced air transport for the fines. The use of a hogger for initial size reduction followed by a pulverizer or ball mill is found a highly efficient manner to achieve the desired feed size. Obviously, when the nature of the feed stock is such that the hogger is not required, the feedstock can be introduced directly into the pulverizer and hence to storage or to pyrolyzer input hopper. Obviously, feedstock that arrives at the site in already powdered condition may be fed directly into the hopper or fines silo without any size reduction.

Each of the aforesaid pieces of equipment will preferably be provided with appropriate controls and interlocks to insure safe and reliable operation using well known technology which need not be detailed here.

It should be noted however that the interlocks will be synchronized in any case to prevent the silo feeder from operating when the silo is full and to prevent the hogger and pulverizer from operating unless the silo feed blower is already operating. Further, the operating sequence will require the pulverizer to be running before the hogger can be started and the hogger to be running before its feed conveyor can be operated.

To interrupt the cycle, the stop sequence will be the reverse of the start up so that the feed conveyor is stopped first followed by the hogger, then the pulverizer, and finally the silo feed blower. When the silo reaches a preselected level of fullness, the silo feed blower will trip which will initiate the tripping of all of the upstream equipment in the sequence described. In a similar fashion, a jam in any intermediate equipment will trip the jammed piece and all equipment upstream from the jam site.

A number of feed stocks have been found suitable in the practice of the present invention such as agricultural crops, forest residue, agricultural and/or industrial waste, and synthetic polymeric waste. The following materials are presented as representative of feed stocks appropriate for use herewith but it is not intended to exclude any material not listed herein which otherwise meets the basic criteria for a feed stock as defined hereby in Table A. Thus, the following materials have been found to be suitable feedstocks, the scientific name being listed parenthetically after the common name where appropriate: Euphorbia lathyris, Candelilla bagasse (Euphorbia antisyphilitica), Raw guayule (Parthenium argentatum) Guayule resins (Parthenium argentatum) Guayule bagasse (Parthenium argentatum), Guayule cork (Parthenium argentatum), Greasewood (Sarcobatus vermiculatus), Jojoba meal (Simmondsia chinensis), Almond hulls (Terminalia catapa), Almond prunings (Terminalia catapa), Sugarcane bagasse (Saccharum officinarum), Wheat straw (Triticum aestivum), Creosote bush (Larrea tridentata), Fir bark (Pseudotsuga menziesii), Arizona cypress (Cupressus arizonica), Pringle manzanita (Arctostaphylos pringle), Wright silktassel (Garrya wrightii), Pointleaf manzanita (Arctostaphylos pungens), Shrub live oak (Quercus turbinella), Hairy mountain mahagony (Cercocarpus breviflorus), Utah juniper (Juniperus osteosperma), Pinyon pine (Pinus edulis), Velvet mesquite (Prosopis guliflora var. relutina), ECO FUEL II (municipal preprocessed refuse), Raw kelp, Kelp residue, Smiling sumac (Rhus copallina), Smooth sumac (Rhus copallina), Red tatarianahoneysuckle (Lonicera tatarica), Giant ragweed (Ambrosia trifida), Pokeweek (Phytolacca amerciana), Tall boneset (Eupatorium altissimum), Rosin weed (Silphium integrifolium), Tall goldenrod (Solidago altissima), Sassafras (Sassafras albidum), Coral berry (Symphoricarpos orbiculatus), Wild bergamot (Monarda fistulosa), Russian thistle (Salsola kali), Water hyacinth (Hyacinthus spp.), Common milkweed (Asclepias syriaca), Swamp milkweed (Asciepias incarnata), Peat (Spagnum spp.), Portuguese oak cork (Quertus subar), Silver maple (Acer saccharinum), Yellowleaf silktassel (Garrya flavescens), Sweet sorghum (Sorghum saccharatum), Pale Indian plantain (Cacalia atriplicifolia), Tall bellflower (Campanula americana), Cherry elaeagnus (Elaeagnus multiflora), Grass leaved goldenrod (Solidago graminifolia), Common elder (Sambucus canadensis), Canada wildrye (Elymus canadensis), Field thistle (Cirsium discolor), Sow thistle (Sonchus oleraceus), Compass plant (Silphium laciniatum), Canaigra roots (Rumex hymenosepaalus), Cut leaf tessel (Dipsacus laciniatus), Blue tessel (Dipascus sylvestris), American germander (Teucrium canadense), Woody milkweed (Asciepias spp.), Rotund-leaf milkweed (Ascelpias spp.), Cotton seed meat (Gossipium thurberi), Cotton seed (Gossypium thurberi), Cotton seed lint (Gossypium thurberi), Cotton seed meal (Gossyspium thurgberi), Cotton seed hulls (Gossyspium thurberi) Cotton gin trash (Gossypium thurberi), Skunkbush (Rhus trilobata), Yerba-santa (Eriodictyon angustifolia), Fourwing saltbush (Atriplex canescens), Netleaf hackberry (Celtis reticulata), Catclaw mimosa (Mimosa biuncifera), Sewage sludge, Corn starch, Coal, Polyethylene, Polypropylene, Lignin, Saw dust, Paper chips, Hog fuel, Mesquite (Prosopis torreyana), Calotropis (Calotropis procera), Rice hulls, Black greasewood (Sarcobatus vermiculatus), Whorled milkweed (Asclepiss verticillata), Stiff leaved goldenrod (Solidago rigida), Ironweed (Vernonia missurica), Toother spurge (Euphorbia dentata), Weeping willow (Selix babylonica), Carpenter's square (Scrophularia marilandica), Aspen (Populus), Locust (Robinis).

TABLE A

| FEEDSTOCK CHARACTERISTICS (dry basis) | |
|---|---|
| HEATING VALUE, Btu/lb | 7,400–12,700 |
| Component | Weight percent |
| Ash | 0.1–35.9 |
| Protein | 0.1–25.3 |
| Polyphenol | 0.1–20.2 |
| Oil | 0.03–9.20 |
| Hydrocarbons | 0–10.4 |
| Suberin | 0.5–26.6 |
| Lignin | 7.8–28.8 |
| Cellulose | 17.7–46.7 |
| Lipids | 5.1–14.9 |
| ELEMENTAL ANALYSIS | |
| C | 37.7–60.9 |
| H | 4.7–8.8 |
| O | 28.9–54.4 |
| N | 0.3–1.7 |
| S | <0.01 |

The granulated feedstock, prepared and stored in the manner described, is introduced as desired from the feeder into the pyrolyzer which converts the biomass into a synthesis gas containing carbon monoxide, hydrogen and olefin rich gas in the manner to be now described.

As shown in the drawing, ground biomass is fed by suitable means such as a hopper, a transfer screw or the like into the pyrolyzer feed mechanisim which delivers the material at a controllable rate into the fluidized bed zone of pyrolyzer. Analysis of typical synthesis gas composition is shown in TABLE B, below.

TABLE B

| SYNTHESIS GAS COMPOSITION (mole %) | | |
|---|---|---|
| Element | Range | Typical |
| Hydrogen | 10–53 | 30 |
| Carbon Monoxide | 6–60 | 30 |
| Olefins | 5–39 | 15 |
| Paraffins | 6–33 | 15 |
| Carbon Dioxide | 4–26 | 10 |

By utilization of specific catalysts and predetermined steam rates, the pyrolyzers are capable of converting unburnt carbon or char and excess Fischer-Tropsch gas into thermal energy by fluid bed combustion.

The combustion heat is transferred to the fluid bed pyrolzyer and sustains the desired pyrolysis temperature as will hereinafter appear. Further the process provides for the recovery of sensible heat from the pyrolysis gas and combustion flue gas which is then employed to generate the steam required for pyrolysis while cleaning the pyrolysis gas for subsequent compression and Fischer-Tropsch synthesis as will appear, the process herein described is an environmentally acceptable neighbor because the combustor flue gas is adequately cleaned prior to atmospheric entry.

As shown in the drawing, the major pieces of equipment in the pyrolyzer section are pyrolyzer and regenerator vessels which are normally equipped with internal gas sparge rings and cyclones. (Not shown) In one practice, the dense phase lift legs will be suspended and will extend about 20 feet below the vessel bottom supports.

As previously described, a suitable charge of biomass material is fed into the pyrolyzer at a controlled rate and delivered into the fluidized bed zone of the pyrolyzer. Recycle gas is used to provide a positive differential pressure between the feed mechanism and the pyrolyzer and to prevent the infiltration of unwanted air into the pyrolysis side of the process. To fluidize the bed of catalyst/heat transfer media/biomass, recycle gas and steam are introduced into the sparge ring under flow control. The gas bubbles lift and disperse the media forming a bubbling bed which promotes intimate contact among the various media at the nominal design temperature of about 1,200–2,000° F., preferrably 1,400°–1,500° F., and a pressure of about 3–4 psig. Pyrolysis gas passes upward into the disengaging space. A cyclone mounted in the disengaging space removes the larger particles entrained in the pyrolysis gas. A secondary external cyclone of the same size removes additional entrained particles and returns the material to the pyrolyzer through a dense phase return leg. Hot pyrolysis gas proceeds to the heat recovery/gas cleanup train. Pyrolysis bed temperature is controlled by adjusting the flow rate of heat medium return to the pyrolyzer from the heat medium supply pot. Recycle gas provides the motive force for transfer of heat medium up the vertical dilute phase lift leg. The pyrolyzer fluid bed height is controlled (differential pressure) by adjusting the heat medium flow out of the pyrolyzer through the dense phase transfer leg into the heat medium return pot. Compressed air is used to return the cooled medium to the regenerator through the vertical dilute phase lift leg. The hydrogen to carbon monoxide ratio and olefin content of the pyrolysis gas are adjusted to the desired value by manipulating the steam to carbon ratio, the pyrolyzer bed temperature, and through the use of catalysts such as dolomite and the like as will hereafter be explained in greater detail.

The regenerator is identical in size and general configuration as the pyrolyzer. During normal operation, recycle gas and outside air are sparged under flow control into the regenerator through a sparge ring. The bed operating temperature is in the range of 1,600°–1800° F. perferably about 1,700° F. Residual char from the biomass is transferred along with the heat carrier medium (normally, alumina) up the left leg to the regenerator. The carrier material is heated by burning recycle gas and char. Bed temperature is controlled by adjusting the inlet recycle gas flow. Ash is removed periodically to prevent excessive solids buildup in the regenerator. Ash is withdrawn near the top of the regenerator bed and discharges into a pot where a water spray quenches the material. Ash slurry is loaded into drums for offsite disposal. The heat carrier can be removed from the heat medium supply pot when the unit is in a cold shutdown mode. Heat medium/catalyst can be loaded into the pyrolyzer via the biomass feed system.

The regenerator contains one internal cyclone for gross particulate removal. A second, exterior cyclone removes most of the carryover solids from the first stage cyclone. The hot flue gas then is routed to a steam superheater for heat recovery.

During start-up of the regenerator/pyrolyzer, natural gas is combusted in an external burner with the combustion gases entering the regenerator sparge ring. The gases fluidize the bed and heat up the carrier medium. Auxiliary steam is sparged into the pyrolyzer to fluidize the bed and provide some initial heating. When the pyrolyzer bed temperature is high enough to sustain the desired pyrolysis reactions, biomass feed will be introduced into the pyrolyzer. Pyrolysis gas will be flared initially. As gas production increases, the gas will be diverted into the waste heat boiler/scrubber train for cleanup and compression. Gas recycle to the pyrolyzer and regenerator will commence as the natural gas and steam flow rates are reduced to bring the pyrolysis/generator units to the desired operating condition.

Shutdown will involve shutoff of biomass feed and gradual reduction of recycle gas flow to the pyrolyzer while maintaining steam for fluidization. Recycle gas flow to the conbustor is shut off while maintaining air for flow fluidization and residual char burn up. Air and steam cool the heat medium below pyrolysis (and combustion) temperatures. When the bed temperatures are cool enough, fluidization steam/air flows are reduced to permit the beds to slump into the dense phase mode (cold shutdown condition).

Pyrolysis gas must be cooled and cleaned prior to compression for the catalytic reactor (Fischer-Tropsch) synthesis. A waste heat boiler is used to reduce the pyrolysis gas temperature to about 575° F. from 1,400° F. Boiler feed water is added to the shell on level control. Steam temperature is set by pressure control at the steam outlet on the top of the boiler. The boiler blowdown rate is controlled manually. Although it is desirable to reduce the flue gas temperature as much as possible to recover usable heat in the form of process steam, care should be exercised to avoid condensing tar-like material in the tubes which will cause fouling.

Partially cooled pyrolysis gas enters the inlet section of a venturi-ejector while cooling water at 85° F. is sprayed through a nozzle into the gas stream to cool the gas to 120° F. and scrub out residual small size particulates. The gas-water mixture enters a cyclonic separator and clean, saturated pyrolysis gas passes upwardly through a wire mesh mist eliminator to the suction side of the pyrolysis gas compressor. A pressure controller on the gas exit line from the column maintains a positive pressure on the entire pyrolysis gas train. Scrubber water flows on level control into a tank located below the disengaging column to cool the pyrolysis gas to 120° F. and condense the excess water vapor in the gas. The warm scrubber water is pumped on level control back to the cooling tower for heat rejection.

Hot flue gas at about 1,700° F. passes through a vertical steam superheater unit which heats the 1540 psig process steam from the waste heat boiler plus additional steam from the auxiliary boiler to about 700° F. for use in pyrolysis vessel. The flue gas exit temperature will depend upon the amount of steam being superheated. Flue gas flows downward through the tubes in the tube bundle. Superheated steam flows upward through the shell side. Partially cooled flue gas is then piped into the flare header under pressure control. Any excess steam is routed to a condenser in the Fischer-Tropsch section as will be described later. Both flue gas and pyrolysis gas can be routed to the flare system upstream of the superheater and waste heat boiler.

The pyrolysis gas and the recycle gas are compressed to a pressure of about 140–500 psig for the Fischer-Tropsch synthesis.

The liquefaction equipment further removes the heat of reaction and maintains a stable operating condition in the reactor while converting carbon monoxide, hydrogen gas and some of the olefins into the desired fuel product using Fischer-Tropsch liquefaction reactions in a slurry phase reactor.

As shown in the drawing, the major piece of equipment in the Fischer-Tropsch liquefaction section is the Fischer-Tropsch reactor. While not shown in the drawing, in my preferred practice, a second Fischer-Tropsch slurry phase reactor is connected in parallel to the reactor shown to facilitate changeover, that is, one reactor can be cleaned and reloaded while the other is in its operation mode.

The unseparated synthesis gas is fed to the second stage (Fischer-Tropsch) reactor containing a catalyst. In this reactor, the reactive components of the feedgas, that is, carbon monoxide, hydrogen, olefins, are converted to a condensable diesel type fuel (essentially $C_7$–$C_{17}$ paraffinic hydrocarbons), free of any significant quantity of oxygenated compounds. A second immiscible phase consists essentially of a binary of normal propanol and water. The remaining gases from the liquid fuel synthesis step are recycled back to the liquifaction reactor inlet or the pyrolyzer, depending upon the composition of the gas.

Thus it has been found that the use of sand, dolomite and catalyst heat transfer media with steam plus off gas from the liqufaction reactor will, at about 1 psig and 1500° F. allow the gasification system to provide 85% conversion of biomass feedstock to a gas having the composition (in mole percent) of: 15%, olefins; 30%, hydrogen; 30%, carbon monoxide; 15%, paraffinic hydrocarbons; and 10%, carbon dioxide.

The liquefaction system, using a $Co/Al_2O_3$ catalyst which has been calcined at 400° F. for 4 hours and reduced with hydrogen at 750° F. for 3 hours at 1 atm will, when disposed in the fluidized bed at 500° F. and 140 pspi, produce a synthesis gas consisting of (in mole percent): 15%, olefins; 30%, hydrogen; 30%, carbon monoxide; 15%, paraffinic hydrocarbons; and 10%, carbon dioxide when the single pass residence is 15–30 seconds and the recycle is conducted at 3/1. The overall operation produced No. 2 diesel fuel at the rate of 40–50 gallons per ton of biomass feedstock (dry, ash free).

Catalyst as used herein refers to those materials generally recognized as useful in the conversion of olefins into paraffinic hydrocarbons in Fischer-Tropsch reactors. Generally, such a catalyst will comprise an active ingredient selected from the group consisting of cobalt, ruthenium, nickel and iron, which is deposited upon or impregnated into a compatible support structure which is formed of alumina, silica, kiesulguhr, diatomaceous earths, and like materials which provide an appropriate surface area and sufficient porosity to accomplish the desired result. Cobalt impregnated into alumina will be used herein to represent the various catalysts known to effect the desired conversion of olefins to paraffinic hydrocarbons. The process hereof is not intended to be limited to any specific catalyst support structure but rather embraces all of the supports which when impregnated with the active ingredient are known to achieve the desired reaction in a Fischer-Tropsch reactor.

The present process further contains a waste treatment section which is designed to collect and treat all of the facility's aqueous waste streams. Treated effluent must be acceptable for continuous, routine discharge into municipal sewer systems and conform to all health standards. Waste solids must also be in a form that is suitable for disposal in a local landfill.

As shown, the wastes produced hereby are combined in a 500 gallon capacity sump and pumped on level control to an extended aeration packaged waste treatment unit. A unit which will provide 24 hours hydraulic retention time in the aeration section is adequate to convert degradable organics into $CO_2$, water and new biological cells. While the combined waste feed may have a BOD level as high as 2,000 mg/l, biological solids concentration in the aeration section will be maintained at about 5,000 mg/l. Minimum BOD reduction will be 92.5 percent at this organic loading. The package unit will also have a clarification section, a clear well and a sludge chamber. The treated effluent is acceptable for reception in a municipal sewer system.

Waste biological sludge is accumulated in a sludge chamber and periodically pumped to a small leaf filter to concentrate the solids for disposal in a sanitary landfill. The filter cake is manually dumped into plastic lined steel drums for disposal. Less than one drum per day of sludge will be produced under normal operating conditions.

To further aid in the understanding of the present invention and not by way of limitation, the following examples are presented.

EXAMPLE 1

In a pilot unit built to demonstrate the feasibility of the present invention while processing ten tons of feedstock per day, the fluidized bed in the pyrolyzer is operated at about 1,450° F. (788° C.) and a pressure of about 3–4 psig. Comminution equipment capable of grinding 3-4 tons of biomass per hour is capable, in four 8-hour shifts, of producing sufficient particulate biomass to maintain the system in full operation (7-24 hour days). The pyrolysis gas is passed upwardly at about 2.5 feet per second. The pyrolysis gas is then cooled to about 575° F. using a fired-tube type boiler capable of generating about 1200 lb/hr of steam at 150 psig using a tube bundle having about 250 square feet of heat transfer surface.

The pyrolysis gas is thereafter further cooled from 575° F. to about 120° F. using a scrubber tank (8 feet diameter by 6 feet high) located below the disengaging column. About 175 gpm of water is required to cool the pyrolysis gas from 575° F. to 120° F. and condense any excess water vapor in the gas.

The twin Fischer-Tropsch reactors have a 4.5 foot diameter by 16 foot straight side lower section and a 6 foot diameter by 6 foot straight side upper section. A small steam drum is located in between and slightly above the two reactors. A 250 square foot condenser, a 30 inch diameter by 8 foot T-T knockout drum, and a 25 inch diameter by 42 inch T-T phase separator make up the bulk of the product handling equipment. The compressor system consists of a two-stage liquid seal pyrolysis gas compressor and two reciprocating recycle gas compressors with a 4.5 foot diameter by 8 foot T-T gas surge drum receiving the combined compresses gas stream.

The batch catalyst handling system consists of two 48 inch diameter by 6 foot T-T jacketed tanks, each equipped with a top mounted agitator. A small pressure filter is provided to remove residual spent catalyst from the carrier medium.

In practice, about 350 ACFM (actual cubic feet per minute) of pyrolysis gas is compressed to 150 psig in two stages using water-sealed type compressors. Recycle gas at about 50 psig is compressed in a two-stage reciprocating compressor to 150 psig and blended with pyrolysis gas in a surge drum. A second two-stage standby reciprocating compressor is available for pyrolysis gas and/or recycle gas compression. Compressed gas is fed on flow control into the bottom of one of the two Fischer-Tropsch reactors. The gas distributor is a perforated plate with $\frac{1}{8}$ inch diameter holes. The gas passes through the distributor forming small bubbles which agitate and expand the catalyst/carrier oil slurry bed promoting mass transfer between the gas and solid catalyst phase.

The reactor operating temperature is 500° F. and the overall Fichser-Tropsch reactions are exothermic. Each reactor contains a 16 foot long vertical tube bundle with about 100 square foot of heat transfer area. The bundle with top and bottom headers form an annulus in the reactor with gas flow parallel to the tubes. Heat is removed from the slurry/gas phase by vaporization of water in the tubes with natural circulation of water from the steam drum to the lower header of the tube bundle. Reactor temperature is controlled by automatically adjusting the steam pressure in the steam drum so that the heat removed by water vaporization is sufficient to maintain the reactor set point temperature. The maximum design pressure in the drum is 600 psig (480° F.). The generated steam is sent to the excess steam condenser and the condensate is returned to the boiler feedwater system.

The tube bundle can also be used for cooling the slurry in the reactor during the shutdown by circulating cooling water through the tubes. During the start-up, auxiliary 150 psig steam and superheated steam can be used to heat up the slurry in the Fischer-Tropsch units.

Fischer-Tropsch product gas passes through a small cyclone designed to knock out any slurry carryover from the reactor. Reactor pressure drop and slurry phase interface level are monitored to detect unstable conditions (e.g., slugging flow) in the reactor. A back pressure controller downstream of the cyclone maintains the desired reactor pressure. Product gas at 500° F. flows into the product condenser which condenses the higher boiling components produced by the Fischer-Tropsch reactions. The cooling water flow rate is controlled to maintain the desired outlet temperature of the Fischer-Tropsch vapor/condensate stream. The condensate and non-condensible vapors pass through a pressure reducing valve to a knock-out drum.

Vapor/liquid separation in the drum occurs at about 50 psig. A mist eliminator minimizes liquid droplet carryover in the vapor to the recycle gas compressor. A takeoff line upstream of the compressor suction provides a recycle gas supply at 50 psig to the pyrolysis section.

The Fischer-Tropsch condensate stream from the knock-out drum consists of a paraffin-rich hydrocarbon phase and an alcohol-rich aqueous phase. Separation of the two-phase mixture is accomplished at atmospheric pressure in a horizontal phase separator. By means of level control and interfacial level control, the hydrocarbon phase is pumped to one of the Fischer-Tropsch product day tanks while the alcohol-rich aqueous phase is pumped to another storage tank. The separator is equipped with vertical baffle sections to prevent intermingling of the phases at the discharge nozzles.

A second off-line Fischer-Tropsch reactor is included to permit draining of the catalyst slurry after a run and preparing a new catalyst/slurry batch for a subsequent run without having to shutdown the Fischer-Tropsch section. Two 600 gallon jacketed tanks are provided for filling and draining catalyst from the off-line reactor. Fischer-Tropsch catalysts will be prepared off site and shipped to the facility in drums or bags. Carrier media will be shipped to the facility in drums (if liquid) or cartons (if solid, e.g., petroleum wax). Petroleum wax is currently the carrier of choice.

A nominal 500 gallon batch of catalyst slurry is prepared by slowly dumping into a first jacketed tank a few 11 pound slabs of wax while feeding 20 psig steam to the jacket of the mix tank. When enough wax melts (about 143° F.), the agitator is turned on and the rest of the required amount of slabs are added to the tank while heating is continued. Then catalyst is added to the liquid to make up a slurry of the desired catalyst concentration. This batch of slurry is pumped into the off-line reactor and the pump is used to circulate slurry in the reactor while the next 500 gallon batch is prepared. Normally, steam would be supplied to the Fischer-Tropsch tube bundle during the loading and holding period to keep the wax above its melting point. The catalyst is kept in suspension either by externally circulating the slurry or by sparging nitrogen, hydrogen or air into the bottom of the reactor.

Hydrogen is used to reduce the cobalt-type catalysts in the Fischer-Tropsch reactor. Reduction is accomplished at the nominal reactor design temperature (500° F.) and pressure (140-150 psig). Hydrogen gas is supplied from cylinders. The standby gas compressor can be used to recycle hydrogen off-gas to conserve hydrogen.

When the Fischer-Tropsch catalyst activity has declined sufficiently to warrant replacement, the spent catalyst/carrier slurry (reactor in shutdown mode) is drained in 500 gallon increments into a 600 gallon agitated settling tank. The agitator is then shut off to allow the catalyst to settle out. Steam in usually maintained in the jacket to keep the slurry temperature above 150° F. When a mud layer has accumulated on the bottom of the tank, the catalyst mud is pumped to a drum and the drummed catalyst mud is shipped off-site for reclamation/regeneration. When the mud layer has been removed, the remaining liquid in the settling tank is pumped through a pressure filter to remove any suspended catalyst particles from the carrier liquid. The filtered carrier can be returned to the slurry mix tank for reuse or drummed out if the carrier is to be replaced. This procedure is repeated until the offline reactor is empty. Cleaned carrier liquid can be recharged to the reactor for wash out if a thorough clean-out of the reactor is desired.

Catalyst regeneration is accomplished when exigencies require by duplicating the aforedescribed equipment and process cycles.

Finally, the hydrocarbon layer of the Fischer-Tropsch liquid product is pumped to one of two 500 gallon capacity day tanks for storage. The daily production is well mixed in the day tank by a pump-around circuit, then a sample is taken for quality analysis to insure that specifications are met. Normally, the day tank's content is pumped to one or more 10,000 gallon diesel product storage tanks for storage and thereafter loaded into tank trucks for delivery and use.

The aqueous alcohol layer of the Fischer-Tropsch liquid product is pumped to a 2,000 gallon aqueous alcohol storage tank for storage pending further handling.

EXAMPLE 2

The system of Example 1 was operated using almond prunings as the biomass feed stock. The fuel produced thereby was analyzed against Commercial No. 2 Diesel Fuel Oil. The results are shown in Table C below.

TABLE C

| PROPERTIES | NO. 2 DIESEL | ALMOND PRUNINGS |
|---|---|---|
| Specific gravity | .8360 | .7902 |
| Gravity, API° | 37.8 | 47.6 |
| Boiling point range, °F. | | |
| evaporated at 10% | 369 | 235 |
| evaporated at 50% | 458 | 352 |
| evaporated at 90% | 563 | 471 |
| Calculated cetane index | 45.9 | 45.3 |
| Heating value, Btu/lb | 19383 | 19354 |

EXAMPLE 3

The fuel produced in Example 2 was analyzed against commercial Kerosene and the results are reported in Table D below.

TABLE D

| PROPERTIES | KEROSENE | ALMOND PRUNINGS |
|---|---|---|
| Specific gravity | .8108 | .7902 |
| Gravity, API° | 43 | 47.6 |
| Boiling point range, °F. | | |
| evaporated at 10% | 336 | 235 |
| evaporated at 50% | 410 | 352 |
| evaporated at 90% | 479 | 471 |
| Calculated cetane index | 47.8 | 45.3 |
| Heating value, Btu/lb | 21676 | 19354 |

EXAMPLE 4

The fuel produced in Example 2 was analyzed against commercial grade JP-4 jet fuel and the results are reported in Table E below.

TABLE E

| PROPERTIES | JP-4 | ALMOND PRUNINGS |
|---|---|---|
| Specific gravity | .7586 | .7902 |
| Gravity, API° | 55 | 47.6 |
| Boiling point range, °F. | | |
| evaporated at 10% | 147 | 235 |
| evaporated at 50% | 302 | 352 |
| evaporated at 90% | 438 | 471 |
| Calculated cetane index | 48.3 | 45.3 |
| Heating value, Btu/lb | 22440 | 19354 |

EXAMPLE 5

The process of Example 1 was performed using Guayule Bagasse as the biomass feed stock. The fuel produced thereby was analyzed agains Commercial No. 2 Diesel Fuel Oil. The results are reported in Table F below.

TABLE F

| PROPERTIES | NO. 2 DIESEL | GUAYLE BAGASSE |
|---|---|---|
| Specific gravity | .8360 | .7950 |
| Gravity, API° | 37.8 | 46.5 |
| Boiling point range, °F. | | |
| evaporated at 10% | 369 | 238 |
| evaporated at 50% | 458 | 414 |
| evaporated at 90% | 563 | 535 |
| Calculated cetane index | 45.9 | 55.7 |
| Heating value, Btu/lb | 19383 | 21043 |

EXAMPLE 6

The fuel produced in Example 5 was analyzed against commercial kerosene and the results are reported in Table G below.

TABLE G

| PROPERTIES | KEROSENE | GUAYLE BAGASSE |
|---|---|---|
| Specific gravity | .8108 | .7950 |
| Gravity, API° | 43 | 46.5 |
| Boiling point range, °F. | | |
| evaporated at 10% | 336 | 238 |
| evaporated at 50% | 410 | 414 |
| evaporated at 90% | 479 | 535 |
| Calculated cetane index | 47.8 | 55.7 |
| Heating value, Btu/lb | 21676 | 21043 |

EXAMPLE 7

The fuel produced in Example 5 was analyzed against commercial grade JP-4 jet fuel and the results are reported in Table H below.

TABLE H

| PROPERTIES | JP-4 | GUAYLE BAGASSE |
|---|---|---|
| Specific gravity | .7586 | .7950 |
| Gravity, API° | 55 | 46.5 |
| Boiling point range, °F. | | |
| evaporated at 10% | 147 | 238 |

TABLE H-continued

| PROPERTIES | JP-4 | GUAYLE BAGASSE |
|---|---|---|
| evaporated at 50% | 302 | 414 |
| evaporated at 90% | 438 | 535 |
| Calculated cetane index | 48.3 | 55.7 |
| Heating value, Btu/lb | 22440 | 21043 |

From the foregoing, it is apparent that a device has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

What is claimed is:

1. A process for producing liquid hydrocarbon fuels consisting essentially of $C_7$-$C_{17}$ paraffinic hydrocarbons free of oxygenated compounds from an oxygen-containing biomass comprising: feeding comminuted biomass into a pyrolyzer heated to a temperature of from about 1,200° to 2,000° F. to produce an intermediate synthesis gas containing in mole percent from 10 to 53 percent hydrogen, from about 6 to 60 percent carbon monoxide, from 5 to 39 percent olefins, from 6 to 33 percent paraffins, and from 4 to 26 percent carbon dioxide; thereafter directing said unseparated intermediate synthesis gas into a catalytic reactor operating at about 500° F. 140 psig, and containing a catalyst consisting of an active ingredient selected from the group consisting of cobalt, ruthenium, nickel and iron disposed upn a compatible support structure selected from the group consisting of alumina, silica, kiesulguhr and diatomaceous earths to form a water/alcohol binary and said liquid hydrocarbon fuel; and separating said liquid hydrocarbon fuel from said water/alcohol binary.

2. A process according to claim 1 in which said biomass is selected from cellulosic and synthetic polymeric materials.

3. A process according to claim 2 in which said biomass contains, by weight percent: 35–62% carbon; 4–9%, hydrogen; 25–55% oxygen; 0.3 to 2%, nitrogen; and less than 0.5% sulfur.

4. A process according to claim 1 in which said catalytic reactor is a Fischer-Tropsch reactor.

5. A process according to claim 4 in which said pyrolyzer contains a fluidized bed.

6. A process according to claim 5 in which said catalytic reactor produces an off gas which is recycled to said pyrolyzer.

7. A process according to claim 6 in which said pyrolyzer is operated at about 1,400° to 1,500° F.

8. A process according to claim 1 in which said intermediate synthesis gas is passed through a cyclone/scrubber system to remove solid particulates and condensible liquids therefrom and thereafter directed to said catalytic reactor.

9. A process according to claim 8 in which said scrubbed intermediate synthesis gas is compressed up to 500 psig prior to the introduction of said compressed gas into said catalytic reactor.

10. A process according to claim 9 in which said catalytic reactor is a Fischer-Tropsch reactor.

11. A process for producing liquid hydrocarbon fuels free of oxygenated compounds from an oxygen-containing biomass comprising: comminuting said biomass; feeding said comminuted biomass into gasification system heated to a temperature of from 1,200° F. to about 2,000° F. to thermally decompose said biomass into an intermediate synthesis gas containing olefins, hydrogen and carbon monoxide; removing particulate solids and condensible liquids from said synthesis gas to clean said gas; compressing said clean gas to up to 500 psig; and directing the compressed gas into a catalytic reactor for liquefaction in the presence of a catalyst consisting of an active ingredient selected from the group consisting of cobalt, ruthenium, nickel and iron disposed upon a compatible support structure selected from the group consisting of alumina, silica, kiesulguhr, and diatomaceous earths to form a water/alcohol binary and a condensible $C_7$-$C_{17}$ paraffinic hydrocarbon fuel; and separating said fuel from said binary.

12. A process according to claim 11 in which said gasification system comprises a pyrolyzer heated to about 1,400°–1,500° F.

13. A process according to claim 12 in which said clean gas is compressed to about 140 psig.

14. A process according to claim 11 in which said biomass is selected from cellulosic and synthetic polymeric materials.

15. A process according to claim 14 in which said biomass contains, by weight percent: 35–62% carbon; 4–9%, hydrogen; 25–55%, oxygen; 0.3 to 2%, nitrogen; and less than 0.5% sulfur.

16. A process according to claim 11 in which said catalytic reactor is a Fischer-Tropsch reactor.

17. A process according to claim 16 in which said pyrolyzer contains a fluidized bed.

18. A process according to claim 17 in which said catalytic reactor produces an off gas which is recycled to the pyrolyzer.

19. A process according to claim 10 in which said pyrolyzer contains a fluidized bed and said Fischer-Tropsch reactor produces an off-gas which is recycled.

20. A process according to claim 19 in which said pyrolyzer is operated at about 1,400° to 1,500° F.

21. A process according to claim 20 in which said biomass contains, by weight percent: 35 to 62% carbon; 4 to 9% hydrogen; 25 to 55% oxygen; 0.3 to 2% nitrogen; and less than 0.5% sulfur.

22. A process according to claim 18 in which said gasification system comprises a pyrolyzer heated to about 1400° to 1500° F. and said clean gas is compressed to about 140 psig.

23. A process according to claim 22 in which said biomass contains, by weight percent: 35 to 62% carbon; 4 to 9% hydrogen; 25 to 55% oxygen; 0.3 to 2% nitrogen; and less than 0.5% sulfur.

* * * * *